United States Patent [19]

Knapp

[11] Patent Number: 4,943,294
[45] Date of Patent: Jul. 24, 1990

[54] POWER-DRIVEN APPLICATOR FOR TAGGING LIVESTOCK

[75] Inventor: Ronald K. Knapp, Cody, Wyo.

[73] Assignee: Y-Tex Corporation, Cody, Wyo.

[21] Appl. No.: 175,493

[22] Filed: Mar. 30, 1988

[51] Int. Cl.⁵ .............................. A61B 17/00
[52] U.S. Cl. ................... 606/117; 606/188; 227/67; 227/130
[58] Field of Search .......... 128/329 R, 330, 316; 40/300, 301; 604/141, 143, 144, 150, 203; 606/116, 117, 185, 188; 227/67, 68, 130

[56] References Cited

U.S. PATENT DOCUMENTS

| | | |
|---|---|---|
| 1,759,400 | 5/1930 | Hobbs . |
| 2,555,133 | 5/1951 | Horstmann . |
| 2,729,063 | 1/1956 | Hoadley . |
| 3,269,630 | 8/1966 | Fleischer . |
| 3,643,649 | 2/1972 | Amato . |
| 3,727,614 | 4/1973 | Kniazak ........................ 604/144 |
| 3,752,161 | 8/1973 | Bent ........................... 128/303 R |
| 3,933,291 | 1/1976 | Stephenson ..................... 227/67 |
| 3,987,570 | 10/1976 | McMurray et al. . |
| 4,146,032 | 3/1979 | Rubenstein et al. . |
| 4,187,708 | 2/1980 | Champoux ....................... 72/30 |
| 4,323,183 | 4/1982 | Duchin . |
| 4,516,577 | 5/1985 | Scott et al. .................... 128/330 |
| 4,536,933 | 8/1985 | Furutsu . |

Primary Examiner—Michael H. Thaler
Assistant Examiner—William Lewis
Attorney, Agent, or Firm—Harness, Dickey & Pierce

[57] ABSTRACT

A tagging device, such as for ears of livestock, driven by a pressurized fluid source is disclosed. The manually controlled pneumatic applicator described utilizes pressurized air for activation to pierce the ear and set the tag as well as retract the piercing element. The applicator is particularly adapted for use with either one-piece or multiple-piece tags.

22 Claims, 3 Drawing Sheets

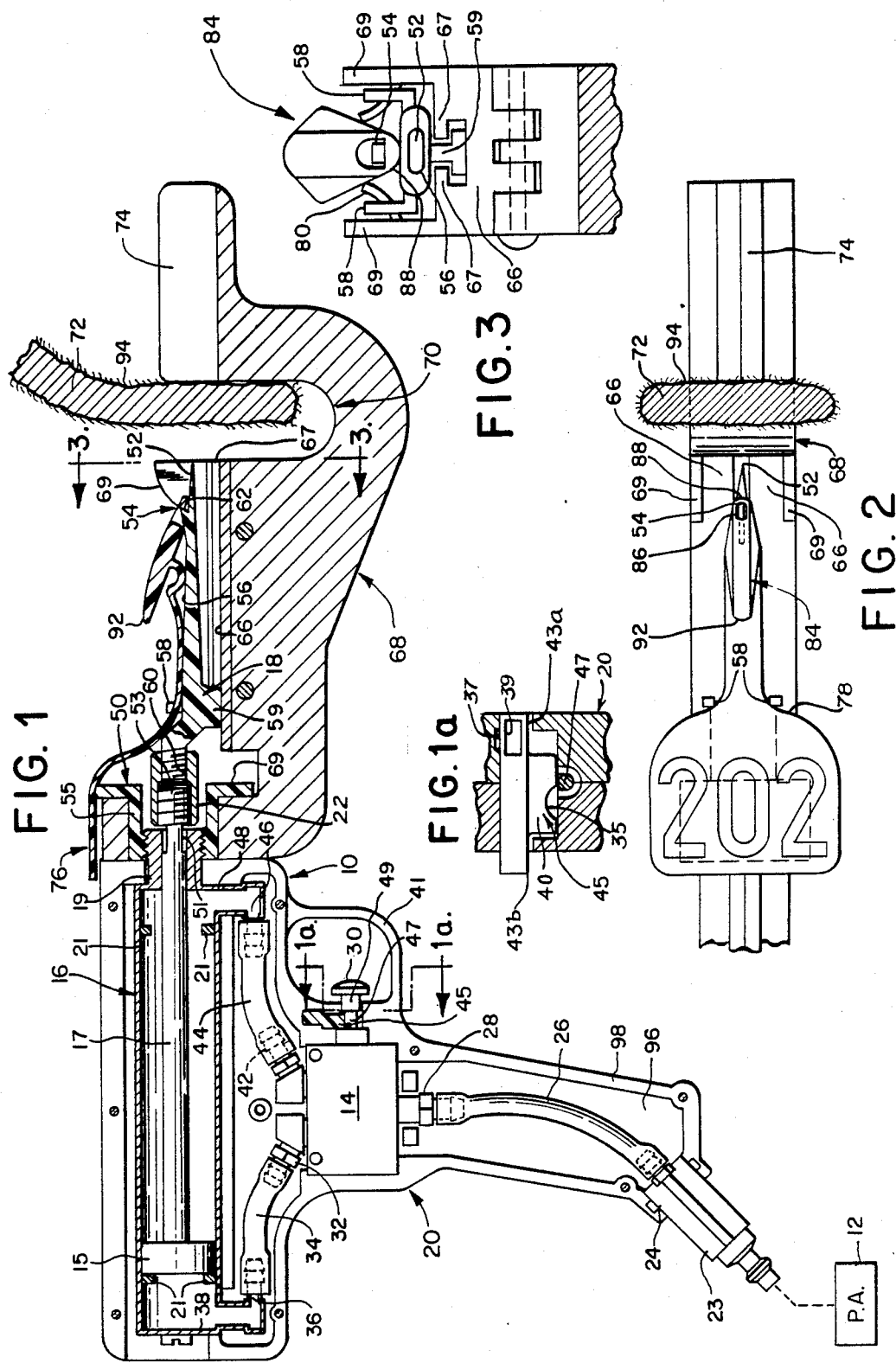

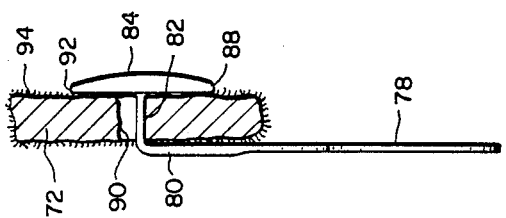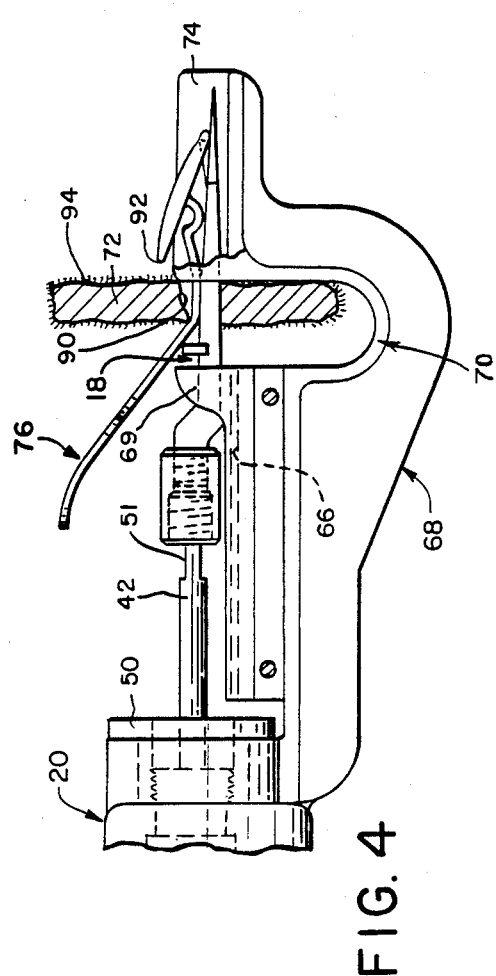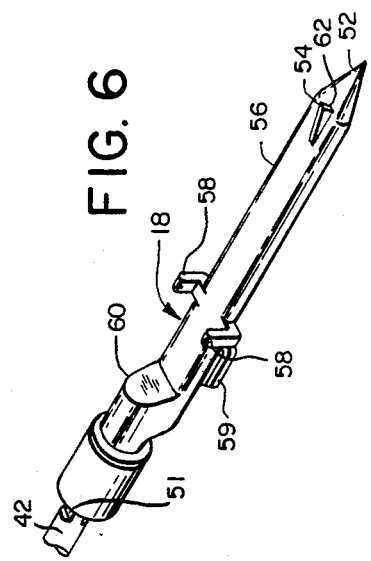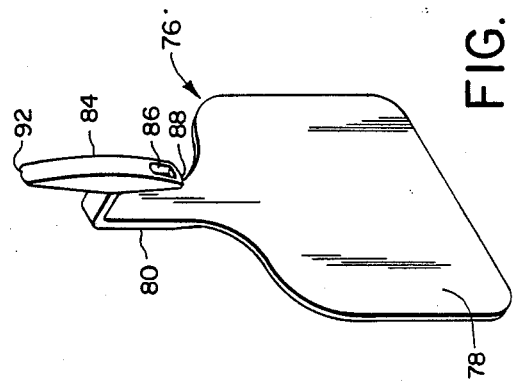

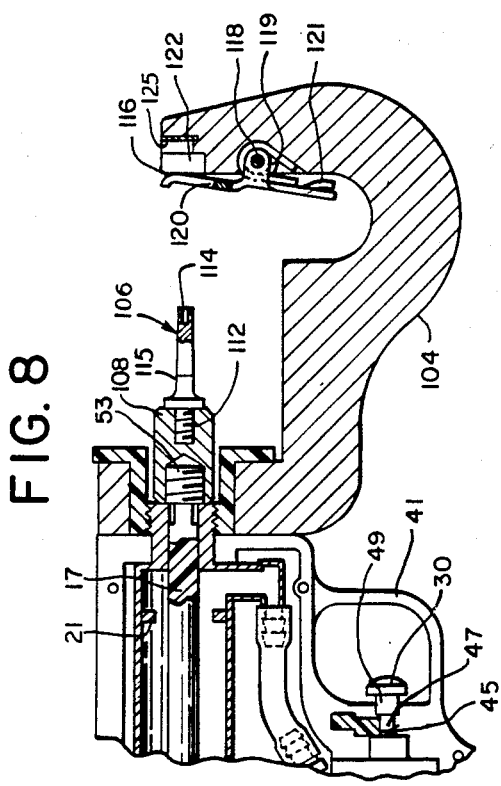

POWER-DRIVEN APPLICATOR FOR TAGGING LIVESTOCK

FIELD OF THE INVENTION

This invention relates to an apparatus for affixing a tag and, more particularly, to a fluid-driven applicator for use in tagging ears of livestock.

BACKGROUND OF THE INVENTION

Plastic tags, such as the type sold by Y-Tex Corporation of Cody, Wyo., under the trademarks E-Z-AP, LONE STAR, and ALL AMERICAN, are widely used for marking livestock, such as cattle, swine, and sheep. Either one-piece or multiple-piece tagging systems are typically used. In a one-piece tagging system, an anchor, integral with the tag, is typically forced through a hole cut in the animal's ear and catches on the back of the ear. In a multiple-piece system, such as a two-piece system, the ear being tagged is pierced and a button applied to rivet the tag in place.

The applicators used to apply or affix the tags have been of two types: a spring-loaded squeeze/plier type, and a knife type. Each of these prior art devices have significant disadvantages. The squeeze/plier-type applicator used primarily with a two-piece tag, causes a significant amount of operator hand strain during repeated application.

With the knife-type applicator, the operator grasps the ear of the animal with one hand, supplying an opposing force, while pushing the blade through the ear with the other hand. The knife-type applicator has at least two significant deficiencies. First, the knife procedure may take longer than the squeeze/plier tagging operation, causing the animal more pain than necessary. In addition, since the animals are conscious and mobile during the tagging operation, the operator runs the risk of stabbing himself, or inadvertently stabbing the animal, during tag application. Operator as well as animal safety is thus a concern.

SUMMARY OF THE INVENTION

The present invention contemplates an improved tagging apparatus, such as for tagging cattle in particular, or for use in other tagging operations. The invention provides improved safety features and reduced hand strain on the operator.

To these ends, the invention comprises: a hand-held device having a piercing element for puncturing the object to be tagged; restraining means for positioning the object to be tagged relative to the piercing means; means for releasably attaching a tag or a tag anchor to the piercing means; a piston which reciprocates to drive the piercing means in and out of the object to be tagged; valve means for controlling the flow of fluid to the piston; and a source of pressurized fluid to drive the device. In one embodiment of the invention, the pressurized fluid is air, supplied either by a compressor or reservoir tank. The tagging device of the invention is further adapted for use with either one-piece or multiple-piece tags, depending on the particular application.

The invention and its advantages will be further understood by reference to the following detailed description of illustrative embodiments of the invention taken in connection with the accompanying drawings, in which:

BRIEF DESCRIPTION OF THE DRAWINGS

FIG. 1 is a side view, substantially in section, of a tagging apparatus for a one-piece tagging system embodying the present invention;

FIG. 1a is a fragmentary sectional view taken along line 1a—1a in FIG. 1;

FIG. 2 is a fragmentary top plan view of the front end of the tagging apparatus of FIG. 1;

FIG. 3 is a sectional view taken along line 3—3 of FIG. 1;

FIG. 4 is a fragmentary side elevational view of the front end of the tagging apparatus of FIG. 1 after ear-piercing;

FIG. 5 is a fragmentary sectional view of a one-piece tag in place after operation of the tagging apparatus;

FIG. 6 is a fragmentary perspective view of the blade portion of the tagging apparatus shown in FIG. 1;

FIG. 7 is a perspective view of a one-piece tag as may be used with the present invention;

FIG. 8 is a fragmentary side elevational view of a tagging apparatus for a two-piece tagging system embodying the present invention;

FIG. 9 is a perspective view of a two-piece tag as may be used with the present invention;

FIG. 10 is a view similar to that of FIG. 8 with a two-piece tag loaded for application;

FIG. 11 is a sectional view 8ear removed) taken along line 11—11 of FIG. 10; and FIG. 12 is a sectional view (ear removed) taken along line 12—12 of FIG. 10.

DETAILED DESCRIPTION OF TWO PRESENTLY PREFERRED EMBODIMENTS OF THE INVENTION

FIG. 1 shows a tagging apparatus embodying the present invention, generally indicated by the reference 10, adapted for a one-piece tag. The tagging apparatus 10 is described below first in terms of its major structural elements, and then its functional elements which cooperate to perform the tagging function.

The primary structural elements of the tagging apparatus 10 are a pressurized fluid source 12, a four-way valve 14, a piston 15 and piston rod 17 within cylinder 16, an interchangeable blade 18 attached via an adapter sleeve 22 to the piston rod 17, and an interchangeable jaw 68. A gun-shaped casing 20, which is adapted to be hand-held, houses or carries these elements.

In this embodiment, the pressurized fluid source 12 is pressurized air. Various pressurized air sources may be used with equally good results within the present invention, including portable or stationary air compressors and portable air tanks or other such reservoirs. Only a very small volume of pressurized air (approximately 0.007 cubic feet) is required for each cycle of operation. The present invention has been found to operate satisfactorily at pressures such as 65 psig for one-piece systems, and 80 psig for two-piece systems.

The valve 14 is a standard two-position, four-way, spool-type valve with spring return, such as Model MJV-4, supplied by Clippard Mfg. Co. of Cincinnati, Ohio. The valve has one input port at 28, two output ports at 32 and 42, and exhaust ports in the valve body. The piston assembly 15, 16 forms a standard double-acting pneumatic cylinder, with a single rod-end 17 and fixed cushions 21, such as a Model CDR-24-3.5B, also supplied by Clippard Mfg. Co. A piston 15 and cylinder 16 with a 1½ inch diameter has been found to work well at the pressures indicated above. The piston cylinder 16 also has an integral stud 19 which supports the piston rod 17 along the stud's inside diameter. The stud 19 has threads on its outside diameter as shown in FIG. 1.

Pressurized air flows to the valve 14 from the pressurized air source 12 through connector 23 and a pathway made up of a standard fitting 24, tube 26, and fitting 28. The valve 14 is operated by trigger 30. When trigger 30 is depressed, valve 14 allows the pressurized air to flow through a pathway made up of a fitting 32, tube 34, and fitting 36, into the rearward portion 38 of piston cylinder 16, driving the piston 15 forcibly forward. When the trigger 30 is released, the pressurized air vents through fitting 36, tube 34, and fitting 32, and then is exhausted through the valve 14 to atmosphere, as described in detail below. Simultaneously, pressurized air is admitted through valve 14 and through fitting 42, tube 44, and fitting 46 into the forward portion 48 of piston cylinder 16 to then drive the piston 15 forcibly rearward.

Trigger 30 has a guard 41 and a trigger safety 45 which prevent the trigger 30 from being accidentally depressed. Trigger 30 has a reduced stem portion 47 and an enlarged stem portion 49 which are adapted to coact with the safety 45. The safety 45 is a standard two-position safety as found in many handguns and power tools and, as shown in detail in FIG. 1a, is comprised of two buttons 43a and 43b that extend through the casing 20 and project from opposite sides of the safety 45. The safety 45 is provided with a lock-out tab 40 which has a semicircular recess 35 formed toward one end thereof that is cofigured to permit the passage of the enlarged stem portion 49 of the trigger 30. When button 43a is pushed and the safety 45 is in a first position (FIGS. 1 and 1a), the tab 40 presents an obstruction to the passage of the enlarged stem portion 49 of the trigger, thus preventing the trigger 30 from being depressed. When button 43b is pushed and the safety 45 is moved to its other position, the semicircular recess 35 in the tab 40 is aligned with the trigger 30, thus permitting the trigger to be depressed. A nub 37 located on the top edge of button 43a is adapted to contact the inner and outer edges of the casing 20 to retain the safety in either of the two positions in which it is placed. The rectangular-shaped hole 39 formed in button 43a permits deflection of the button when the safety 45 is moved.

Piston rod 17 is attached to piston 15 and extends through the forward portion 48 and stud 19 of the piston cylinder 16. Piston rod 17 has flats 51 (FIG. 1) along a portion of its length, adapted to receive a wrench or other such tool, and is threaded at its free end 53.

A collar 50 has inside diameter threads along shaft 55 which correspond with the outside diameter threads on piston cylinder stud 19. Collar 50 also has a radially extending portion 69 which abuts the rearward end of jaw 68, and holds the jaw 68, the casing 20, and the piston cylinder 16 together when the tagger is assembled, as shown in FIGS. 1 and 4. The collar 50 and the jaw 68 are removed simultaneously from the stud 19 by unscrewing the collar 50 from the stud 19, then sliding the collar 50 and jaw 68 off the portion of the piston rod 17 which extends out of the piston cylinder 16 (with the blade removed, as described below). Another and different jaw can then be substituted, as hereafter described.

A horizontal support plate 66 on the jaw 68 (FIGS. 1 and 4) supports the blade 18. The removable support plate 66 has guide rails 67 running along either side which define a "T"-shaped void and are adapted to receive and guide the inverted "T"-shaped runner 59 molded integrally with the blade 18 as described below. The support plate 66 also has kick-off ramps 69 on either side (FIGS. 1–4). The jaw 68 has a slot 70 located forward of the blade 18 which is adapted to receive an animal's ear 72, or other such object to be tagged, as shown in FIG. 1. The jaw 68 also has a channel 74 forward of the slot 70 which is aligned with the blade 18 to receive the blade 18 when the blade is in its forward position, as shown in FIG. 4. The forward portion of the jaw 68 thus serves as a safety shield to prevent the blade 18 from contacting the body of the animal or the operator when extended.

Blade 18 can be molded from plastic and is comprised of a knife point 52, a knob 54, a tapered body 56 of elliptical cross-section, tag retaining tabs 58 and the runner 59 along the blade body 56, and a stepped-up cylindrical base 60 that is threaded into adapter sleeve 22 which is in turn threaded onto the free end 53 of piston rod 17. The knob 54 is generally triangular in vertical cross-section, as best shown in FIG. 6, with an acute angle at point 62 where the knob 54 joins the body 56 of blade 18. Tag retaining tabs 58 are generally "L"-shaped and are molded integrally with the body 56 of the blade 18. As stated above, the runner 59 has an inverted "T" shape and is similarly molded integrally with the blade body 56.

The blade 18 is supported by a removable support plate 66 with guide rails 67 that is mounted to the jaw 68. The guide rails 67 which run along either side of the support plate 66, together define a "T"-shaped void that is adapted to receive the inverted "T"-shaped runner 59 (FIG. 3). The guide rails 67 of support plate 66 prevent both side-to-side and vertical movement of the blade. Only movement in the same direction as the axis of the piston rod 17 (toward and away from the animal's ear) is unrestrained. The support plate 66 has kick-off ramps 69 at the end closest to the knife point 52. The kick-off ramps extend above the tag retaining tabs 58 and are spaced wider apart than the tag retaining tabs 58.

Blade 18 is attached by disconnecting the pressurized air source 12, thereby allowing piston 15 to travel freely in piston cylinder 16, manually pulling at the free end 53 of piston rod 17 to expose the flats 51, pushing the blade 18 with the blade runner 59 between the guide rails 67 of support plate 66, and screwing the piston rod 17 into the threaded hole in adapter sleeve 22 using a wrench or other tool against the flats 51 on piston rod 17 (see FIGS. 1 and 6). The runner 59, held within the guides 67 of support plate 66, restricts the blade 18 from turning while the piston rod 17 and adapter sleeve 22 are screwed onto the blade 18. Blade 18 may be replaced as necessary by unscrewing the adapter sleeve 22 from the base 60 of the blade 18.

A one-piece tag 76, (FIG. 7) can be used with the applicator 10, and is comprised of a relatively large, flat tag face 78 (imprinted with numerals or other symbols on either side), a stem 80, a bridge 82, and an anchor 84. The anchor 84 has a hole 86 located near the edge 88 of anchor 84 which is closest to the tag face 78. Knob 54 is adapted to fit snugly into hole 86. One-piece tags 76 are generally made out of rubber or flexible plastic.

In operation of the applicator 10, the operator bends the tag 76 at the bridge 82 such that the stem 80 and the anchor edge 88 are roughly in line as shown in FIG. 3. The operator places the edge 88 of the tag anchor 84 on the upper edge of the blade 18 forward of the blade knob 54, draws the tag back, fitting the knob 54 into the anchor hole 86. The operator then places the tag stem 80 between tag retaining tabs 58 such that the tag is held in position as shown in FIGS. 1, 2, 3, and 4. The operator positions the animal's ear 72 in the slot 70, moves the safety 45 into the appropriate position and depresses trigger 30.

When the trigger 30 is depressed, the valve 14 directs pressurized air into the rearward portion 38 of piston cylinder 16. This flow of pressurized air drives the piston 15 and piston rod 17 forward, propelling the blade 18, supported by the runner 59 along and within guide rails 67, and the support plate 66. The foremost portion 88 of the tag anchor 84 is pushed through a puncture 90 (FIGS. 4 and 5) made by the blade point 52. The puncture 90 widens until the anchor 84 passes through it. The leading edge 78 of the tag face contacts the kick-off ramps 69 and is forced upward as shown in FIG. 4, releasing the tag stem 80 from the tag retaining tabs 58. The forward motion of the blade 18 stops once the piston 15 reaches the end of its forward travel, contacting the fixed cushions 21 in the forward end of piston cylinder 16. At this time the following edge 92 of the anchor 84 has passed through the puncture 90. Jaw 68 supports the animal's ear. It will be understood that other mechanisms can be used to support the object being tagged, including the mass of the object itself.

When the trigger 30 is released, pressurized air is admitted by valve 14 from the pressurized air source 12 into the forward portion 48 of the piston cylinder 16. The air pressure on the forward face of the piston 15 forces the piston 15 and the shaft 17 towards the rearward portion 38 of the piston cylinder 16, thereby retracting the blade 18. As blade 18 retracts, the following edge 92 of anchor 84 catches on the back side 94 of the animal's ear 72. The anchor 84 is wedged against the back side 94 of the ear 72, forcing the knob 54 free from the hole 86. When the blade 18 is fully retracted from the puncture 90, the anchor 84 remains on the back side 94 of ear 72, with the bridge 82 extending through the puncture 90, as shown in FIG. 5.

When the trigger 30 is either depressed or released, the side of the piston cylinder which is not undergoing pressurization is open to exhaust the trapped air. Thus, air exhausted from piston cylinder 16 travels out through either fitting 46, tube 44, and fitting 42 (with trigger 30 depressed), or fitting 36, tube 34, and fitting 32 (when the trigger 30 is released), and through the four-way valve 14 into a chamber 96 in the shell handle 98. Air exhausts from chamber 96 through ports in the housing (not shown) to the atmosphere. The exhaust of the pressurized air into the shell handle 98 and through the ports to atmosphere muffles the noise of the exhaust to avoid frightening the animal being tagged. Alternatively, a small muffler (not shown) may be set in the wall of the shell handle 98 to reduce exhaust noise. A piece of open-celled, foamed plastic placed in chamber 96 has also been found to reduce the noise.

The tagging device 10 can be easily converted to multiple-piece tagging systems such as a two-piece tagging system by replacing the "one-piece" jaw 68 with a "two-piece" jaw 104, and the blade 18 with an applicator pin 106 (e.g., FIGS. 8 and 10), adapted for use with the "two-piece" tag. A jaw, such as the "two-piece" jaw 104 shown, is attached to the piston cylinder 16 and casing 20 in the same fashion as described for the "one-piece" jaw 68.

As with the adapter sleeve 22 for the "one-piece" system blade 18, sleeve 108 for applicator pin 106 is threaded on its inside diameter to accommodate the threading at 53 on piston rod 17. Applicator pin 106 is replaceable and is threaded at its base 112 to screw into the free end of the sleeve 108 as shown in FIG. 8. The stem of the applicator pin 106 is provided with a gradual taper and a slightly enlarged diameter portion 115 adjacent the flange at the base of the stem to provide a small friction fit with the bore in the button 126 of the two-piece tag to thereby secure the button 126 to the application pin 106. In addition, the end of the applicator pin 106 has a cylindrical-shaped cavity formed therein, as shown at 114, that is adapted to receive and support the button tip 135 of the two-piece tag as shown in FIGS. 10 and 12. In the two-piece embodiment, the sleeve 108 can be made from plastic, aluminum, steel, or other suitable metal, and the applicator pin 106 from hardened or alloy steel.

A clip 116 is attached to the jaw 104 via roll pin 118. Clip 116 has a U-shaped slot 120 (e.g., FIGS. 11 and 12) in line with applicator pin 106, and a torsion spring 119 around roll pin 118 (e.g., FIG. 10).

The clip 116 has a metal tab 121 that limits the maximum movement of the clip 116 and serves to retain the end of torsion spring 119. Jaw 104 has a cavity 122, as shown in FIGS. 8, 10, and 12, that is aligned with the applicator pin 106 and the slot 120 in clip 116 as shown in FIGS. 8 and 10. A "blunt" plate 125, comprised of high carbon, zinc-coated steel, is located on the opposing face of cavity 122 to protect the jaw 104 as described below.

A two-piece tag (FIG. 9) is used with this embodiment of the applicator, and is comprised of a button 126 and a tag body 124. The tag body has a tag face 128, a stem 130, and a female sleeve 132. The button 126 has a hollow male stem 134 molded to a base 136, and a puncturing tip 135 attached to the opposite end of the male stem 134. As best shown in FIG. 12, the puncturing tip 135 is made of metal or a hard plastic and is conically shaped at its exposed end and has a cylindrical rod 137 at its other end which projects into the hollow male stem 134. A flange 139 on the tip component 135 is embedded in the enlarged head portion 140 of the male stem 134 to prevent the tip 135 from separating from the stem 134.

In operation, the operator places the tag body 124 under the clip 116 so that the female sleeve 132 sits in the cavity 122 in jaw 104. The hole in the posterior of the female sleeve 132 is thereby aligned with the U-shaped slot 120 in the clip 116, as shown in FIGS. 11 and 12. The tag stem 130, placed between the clip 116 and the jaw 104, opens the clip 116, deflecting the spring 119 and thereby biasing the stem 130 of the tag body 124 in place. The tab 121 can be bent to limit the distance which the clip 116 opens to accommodate the tag stem 130.

The operator places the button 126 over the applicator pin 106 as shown in FIG. 10. The cylindrical rod 137 projecting from the tip component 135 into the hollow male stem 134 rests in and is supported by the cylindrically shaped cavity 114 in the end of applicator pin 106. The operator then positions the animal's ear 72 in the jaw 104 between the puncturing tip 135 and the clip 116, moves the safety 45 into the appropriate position, and depresses the trigger 30. When the applicator pin 106 is propelled forward as described for one-piece systems above, the opposed conical shape on the puncturing tip 135 punctures the animal's ear 72. The applicator pin 106 also forces the puncturing tip 135 and male extension 134 of the button 126 through the puncture 90, past the U-shaped slot 120 in clip 116, and into the female sleeve 132 in the tag body 124. At the end of the application stroke, the tip 135 of the button 126 strikes the blunt plate 125 in recess 122 and dulls the sharp point of the button. The blunt plate 125 thereby also serves to protect the outer portion of the jaw 104 from being damaged or worn from repeated impact by the sharp tip of the buttons.

When the trigger 30 is released, the applicator pin 106 retracts, leaving the button 126 firmly riveted to the tag body 124. The clip 116, restrained by the tab 121, holds the tag body 124 in place as the applicator pin 106 retracts from the button 126, thereby preventing the tag 124 and button 126 from sticking to the applicator pin 106. The tag body 124, which is now attached to the animal's ear 72, is removed from between the clip 116 and the jaw 104 by pulling the tagger 10 down and away from the ear 72.

Thus, as with a "one-piece" system, an anchor portion of the two-piece tag 124, the button 126, is forced through the object being tagged and holds the tag firmly in place.

The applicator design described above has several features that improve operator safety. When the pressurized air source 12 is connected at connector 23, the air is routed to the piston 15 such that the blade 18 or the applicator pin 106 automatically returns to its retracted position away from possible obstructions. Releasing the trigger 30 also returns the blade 18 or the applicator pin 106 to its retracted position. The trigger guard 41 and safety 45 prevent accidental depression of the trigger 30. The chamber 96 and ports 100, or alternative muffling means, prevent the exhaust of air from making a loud noise that might startle the animal being tagged and cause it to injure the operator.

The tagging device of the present invention has a number of distinct advantages over the prior art. This applicator requires very little effort on the part of the operator. The design also allows an operator to tag livestock quickly, efficiently, and more safely. The tagging device has interchangeable blades and jaws so that it may be used as part of a one-piece or multiple-piece tagging system. Alternate embodiments of the present invention could be used with other tagging systems by using an appropriate blade and jaw. In addition, alternative trigger guard and muffler designs could be used. It has been found, however, that excellent results may be obtained using the embodiments described herein.

Of course, it should be understood that various changes and modifications to the preferred embodiments described herein will be apparent to those skilled in the art. Such changes and modifications can be made without departing from the spirit and scope of the present invention.

What is claimed is:

1. A hand-portable livestock tagging device operable by a pressurized pneumatic fluid source comprising:
   a casing holdable by one hand and having support means for positioning an object on livestock to be tagged;
   a valve means located in said casing for controlling the direction of flow of pressurized pneumatic fluid;
   manually actuable means mounted in said casing and connected to said valve means for controlling the position of said valve means;
   a piston cylinder located within said casing;
   a double-acting piston carried within said piston cylinder and driven fully and rapidly by the pressurized pneumatic fluid in a first direction and in a second opposite direction in accordance with the position of said valve means;
   means for directing the pressurized fluid from said pneumatic fluid source to said valve means and from said valve means to said piston cylinder;
   piercing means connected to and moving with said piston for penetrating the object to be tagged when driven by said piston in said first direction and for retracting from the object when driven by the piston in said second direction; and
   means for attaching a tag having an anchor portion to said piercing means such that the anchor portion of the tag will be forced through the object to be tagged by said piercing means when the piercing means is driven fully and rapidly in said first direction.

2. The tagging device of claim 1 wherein said valve means is a manual, bi-directional, four-way valve having two output ports.

3. The tagging device of claim 2 wherein said manually actuable means comprises a finger trigger.

4. The tagging device of claim 3 further including a trigger guard to prevent accidental depression of said trigger.

5. The tagging device of claim 3 further including a safety to prevent accidental depression of said trigger.

6. The tagging device of claim 3 wherein the pressurized fluid is air.

7. The tagging device of claim 6 wherein said casing further includes means to muffle the exhaust of air from the valve means.

8. The tagging device of claim 7 wherein the means to muffle is comprised in part of a chamber in said casing into which the pressurized air is exhausted.

9. The tagging device of claim 8 wherein the means to muffle is further comprised of two or more ports in said casing through which the pressurized air vents from said chamber to the atmosphere.

10. The tagging device of claim 1 wherein said piercing means includes a knife blade, and further includes piston rod having first end connected to said piston and a second end connected to said knife blade.

11. The tagging device of claim 10 further comprising a means of supporting said knife blade during penetration of the object being tagged.

12. The tagging device of claim 11 wherein said knife blade support means restrain movement of the knife blade in all directions other than toward and away from the object being tagged.

13. The tagging device of claim 10 wherein said knife blade has retaining tabs to support and restrain a tag.

14. The tagging device of claim 13 further comprising tag kick-off ramps which separate the tag from said retaining tabs during movement of said knife blade.

15. The tagging device of claim 10 wherein said support means for positioning an object to be tagged includes a blade jaw having a slot within which the object to be tagged is received, said slot having a rear wall against which the object is supported relative to said knife blade.

16. The tagging device of claim 1 wherein said piercing means includes a puncturing tip, and further includes a piston rod having one end connected to said piston and a free end adapted to carry said puncturing tip.

17. The tagging device of claim 16 wherein said support means for the positioning an object to be tagged includes a blade jaw having a slot within which the object to be tagged is received, said slot having a rear wall against which the object is supported relative to said puncturing tip.

18. The tagging device of claim 1 wherein said piercing means comprises a knife blade and a supported puncturing tip which are interchangeable for use with different tagging systems.

19. The tagging device of claim 1 wherein
said piercing means includes (1) a plurality of piercing members usable one piercing member at a time selected from the group consisting of knife blades and puncturing tips, and (2) a piston rod having first end connected to said piston and a second end connected to one such piercing member then in use,
the support means for supporting an object to be tagged includes first and second blade jaws usable one at a time, with each of the blade jaws having a slot within which the object to be tagged is received, said slot having a rear wall which supports the object relative to one of said piercing members, with the first blade jaw being usable with a knife blade and the second blade jaw being usable with a puncturing tip, and
the tagging device further comprises
means for releasably attaching each of said first and second blade jaws to said casing in interchangeable fashion, and connecting means for releasably attaching said knife blade and puncturing tip piercing members to said second end of said piston rod in interchangeable fashion one at a time
whereby said said tagging device is readily adapted for use with one-piece tagging systems or with multiple-piece tagging systems.

20. The tagging device of claim 1 wherein said support means is a jaw attached to the tagging device which has a rear wall extending behind the object being tagged to thereby support the object relative to said piercing means.

21. A livestock tagging device for use in one-piece tagging operations and operable by a pressurized pneumatic fluid source, comprising:
a housing adapted to be hand held;
a bi-directional four-way valve located in said housing for controlling the direction of flow of pressurized pneumatic fluid;
manually operable trigger means mounted to said housing for directly controlling said four-way valve;
a piston assembly having a piston cylinder located in said housing, a piston and a piston rod connected thereto carried within the piston cylinder, said piston being fully and rapidly driven in a first direction by the application of pressurized pneumatic fluid to one end of said cylinder and in a second opposite direction by the application of pressurized pneumatic fluid to the other end of said cylinder;
means for directing the pressurized fluid from said fluid source to said valve and from said valve to said one end of said piston cylinder and from said valve to said other end of said piston cylinder;
a knife blade means interconnected to an end of said piston rod for penetrating an object on livestock to be tagged;
means for attaching a tag to said knife blade means, said tag including an anchor portion which is forced by said blade means through the object to be tagged; and
a jaw connected to said housing and positionable relative to the object to be tagged during operation of the tagging device;
wherein actuation of said trigger means operates said valve such that said piston is driven in said first direction to drive said knife blade means and then apply said tag, and further wherein releasing of said trigger means operates said valve such that said piston is driven in said second direction to retract said knife blade means.

22. A livestock tagging device for applying a two-piece tagging system comprised of a male tag component and a female tag component and operable by a pressurized pneumatic fluid source, comprising:
a housing adapted to be hand held;
a bi-directional four-way valve located in said housing for controlling the direction of flow of pressurized pneumatic fluid;
trigger means mounted to said housing for controlling said four-way valve;
a piston assembly having a piston cylinder located in said housing, a piston and a piston rod connected thereto carried within the piston cylinder, said piston being fully and rapidly driven in a first direction by the application of pressurized pneumatic fluid to one end of said cylinder and in a second opposite direction by the application of pressurized pneumatic fluid to the other end of said cylinder;
means for directing the pressurized fluid from said fluid source to said valve and from said valve to said one end of said piston cylinder and from said valve to said other end of said piston cylinder;
applicator means affixed to an end of said piston rod for supporting the male tag component adapted to penetrate an object on livestock to be tagged; and
a jaw connected to said housing and positionable relative to an object on livestock to be tagged and including means for supporting the female tag component;
wherein actuation of said trigger means operates said valve such that said piston is driven in said first direction to drive said applicator means so that the male tag component penetrates to object to be tagged and is joined to the female tag component, and further wherein releasing of said trigger means operates said valve such that said piston is driven in said second direction to retract said applicator means.

* * * * *